US008088827B2

(12) United States Patent
Nisato et al.

(10) Patent No.: US 8,088,827 B2
(45) Date of Patent: Jan. 3, 2012

(54) USE OF IRBESARTAN FOR THE PREPARATION OF MEDICINAL PRODUCTS THAT ARE USEFUL FOR TREATING PULMONARY HYPERTENSION

(75) Inventors: Dino Nisato, Saint Georges D'Orques (FR); Alain Roccon, Sainte-Croix-de-Quintillargues (FR); Sylvie Cosnier-Pucheu, Villeneuve-les-Maguelone (FR)

(73) Assignee: Sanofi-Aventis, Paris (FR)

( * ) Notice: Subject to any disclaimer, the term of this patent is extended or adjusted under 35 U.S.C. 154(b) by 4 days.

(21) Appl. No.: 12/477,562

(22) Filed: Jun. 3, 2009

(65) Prior Publication Data
US 2009/0247510 A1 Oct. 1, 2009

Related U.S. Application Data

(63) Continuation of application No. 10/492,804, filed as application No. PCT/FR02/03439 on Oct. 9, 2002, now abandoned.

(30) Foreign Application Priority Data

Oct. 26, 2001 (FR) ...................................... 01 13936

(51) Int. Cl.
*A61K 31/18* (2006.01)
*A61K 31/41* (2006.01)
(52) U.S. Cl. ........................................ 514/601; 514/381
(58) Field of Classification Search .................. 514/269, 514/256, 232.2, 235.8, 365, 381, 601
See application file for complete search history.

(56) References Cited

U.S. PATENT DOCUMENTS

| 5,258,510 | A | 11/1993 | Ogawa et al. |
| 5,270,317 | A | 12/1993 | Bernhart et al. |
| 5,292,740 | A | 3/1994 | Burri et al. |
| 5,292,741 | A | 3/1994 | deLaszlo et al. |

FOREIGN PATENT DOCUMENTS

| EP | 0454511 | 10/1991 |
| EP | 1106210 | 6/2001 |

OTHER PUBLICATIONS

Havranek, E.P., *American Journal of Managed Care*, vol. 7, suppl. No. 4, pp. S374-S376 (1998).
Havranek, E.P., *Journal of the American College of Cardiology*, vol. 5, No. 33, pp. 1174-1181 (1999).
Rosenstock et al., EMBASE No. 1999046413 (1998).
Laurent et al., *Fundamental & Clincial Pharmacology*, vol. 3, No. 10, pp. 243-257 (1996).
Gillis, J.C. et al., *Drugs*, vol. 6, No. 54, pp. 885-902 (1997).
Markham et al., *Drugs*, vol. 5. No. 59, pp. 1187-1206 (2000).
Cassis et al., *J. of Pharmacology & Experimental Therapeutics*, vol. 3, No. 262, pp. 1168-1172 (1992).
Cassis et al., *Biochemical Pharmacology*, vol. 1, No. 54, pp. 27-31, (1997).
Meaney-Mendiolea et al., *Clinical Drug Investigation*, vol. 6, No. 19, pp. 431-439 (2000).
Calderone et al., *Canadian Journal of Cardiology*, Supplement F, No. 16, p. 152F (2000).
McLeod et al., *Drugs*, vol. 31, No. 2, pp. 177-184 (1986).
Medline Database, Abstract No. NLM10556112 (1999).
Robbins et al., *Journal of Applied Physiology*, vol. 85, No. 2, pp. 731-737 (1998).
Van Giersbergen, *Clincial Pharmacology & Therapeutics*, vol. 69, No. 2, p. 67 (2001).
Massart et al., *Journal of Hypertension*, vol. 16, No. 6, pp. 835-841 (1998).
Channick et al., *Lancet*, vol. 358, No. 9288, pp. 1119-1123 (2001).
Huy et al., *Expert Opinion on Investigational Drugs*, vol. 10, No. 11, pp. 1937-1946 (2001).
Windholz, et. al., The Merck Index, 10th Edition, p. 692, abstract No. 4683 (1983).
Eddahibi, S., et al., Protection from pulmonary hypertension with an orally active endothelin receptor antagonist in hypoxic rats, Am J Physiol Heart Circ Physiol 268: vol. H828-H835, 1995; 0363-6135/95.
MayoClinic.com/health/pulmonay-hypertension/DS00430/DSECTION=7, (2007).
Badesch D.B. et al., "Medical Therapy for Pulmonary Arterial Hypertension", *Chest 131*:1917-1928 (2007).
Galiè N. et al., "Guidelines for the Diagnosis and Treatment of Pulmonary Hypertension-The Task Force for the Diagnosis and Treatment of Pulmonary Hypertension of the European Society of Cardiology (ESC) and the European Respiratory Society (ERS), Endorsed by the International Society of Heart and Lung Transplantation (ISHLT)", *European Heart Journal* 30:2493-2537 (2009).
Rich S., "Clinical Insights into the Pathogenesis of Primary Pulmonary Hypertension", *Chest 114*:237S-241S (1998).
Kreutz R. et al., "Effect of Losartan on Right Ventricular Hypertrophy and Cardiac Angiotensin I-Converting Enzyme Activity in Pulmonary Hypertensive Rats", *Clin. And Exper. Hypertension* 18(1):101-111 (1996).

*Primary Examiner* — Kevin E Weddington
(74) *Attorney, Agent, or Firm* — James W. Bolcsak, Esq.; Scully, Scott, Murphy & Presser, P.C.

(57) ABSTRACT

The present invention relates to the use of irbesartan for the preparation of medicinal products that are useful for preventing or treating pulmonary arterial hypertension or pulmonary hypertension.

2 Claims, No Drawings

USE OF IRBESARTAN FOR THE PREPARATION OF MEDICINAL PRODUCTS THAT ARE USEFUL FOR TREATING PULMONARY HYPERTENSION

The present invention relates to a novel use of irbesartan for the preparation of medicinal products that are useful for preparing medicinal products for preventing or treating pulmonary hypertension or pulmonary arterial hypertension.

Irbesartan is an antagonist of the angiotensin II $AT_1$ receptors.

This compound and its mode of preparation are described in patents EP 454 511 and U.S. Pat. No. 5,270,317.

Irbesartan, alone or in combination with a diuretic agent, is indicated in the treatment of various cardiovascular complaints, especially hypertension and diabetic nephropathy.

Pulmonary arterial hypertension or pulmonary hypertension corresponds to an increase in pressure in the pulmonary arterial network to above 35 mmHg; the vital prognosis of this disease is dramatic. During this disease, the caliber of the pulmonary arterials and vessels shrinks and the resulting pressure increase has repercussions on the right ventricle; right ventricular insufficiency is gradually manifested and gets worse.

The effect of losartan, an antagonist of the angiotensin II $AT_1$ receptors, was tested in this disease using an animal model in which the pulmonary hypertension is induced with monocrotaline. Monocrotaline (MCT) is an alkaloid toxin that induces pulmonary vascular impairments leading to the development of pulmonary hypertension, which is the cause of a right ventricular hypertrophy. This evolutive pathology is reflected by a near-total death of the animals within a few weeks. At the terminal stage, the presence of pulmonary edema is noted.

In this model it was found by two different groups of authors that losartan has no effect:
- L. Cassis et al.: J. Pharmacol. Exp. Therap. 1992, 262(3), 1168-1172 and Biochem. Pharmacol., 1997, 54(1), 27-31,
- R. Kreutz et al.: Clin. Exp. Hypertens., 1996, 18(1), 101-111.

It has now been found, surprisingly, that irbesartan is, itself, active on this model of arterial hypertension.

Thus, one subject of the present invention is the use of irbesartan for the preparation of medicinal products that are useful for preventing or treating pulmonary hypertension or pulmonary arterial hypertension.

According to the present invention, irbesartan may also be used in combination with another active principle, for the preparation of medicinal products that are useful for preventing or treating pulmonary hypertension, for example a diuretic agent such as hydrochlorothiazide, an aquaretic agent, such as a vasopressin $V_2$ receptor antagonist, a vasodilator, an anticoagulant, a phosphodiesterase inhibitor, prostacyclin or an endothelin receptor antagonist such as bosentan.

For its use as a medicinal product, irbesartan, a pharmaceutically acceptable salt thereof or a solvate thereof, alone or in combination with another active principle, should be formulated as a pharmaceutical composition.

In the pharmaceutical compositions of the present invention for oral, sublingual, inhaled, subcutaneous, intramuscular, intravenous, transdermal, local or rectal administration, the active principle, alone or in combination with another active principle, may be administered in unit administration form, as a mixture with standard pharmaceutical supports, to animals and human beings. The appropriate unit administration forms comprise oral forms such as tablets, gel capsules, pills, powders, granules and oral solutions or suspensions, sublingual and buccal administration forms, aerosols, topical administration forms, implants, transdermal, subcutaneous, intramuscular, intravenous, intranasal or intraocular administration forms and rectal administration forms.

In the pharmaceutical compositions of the present invention, the active principle(s) is(are) generally formulated in dosage units. The dosage unit contains 50 to 500 mg and advantageously from 75 to 300 mg of active principle per dosage unit, for daily administrations, one or more times a day.

For the treatment of pulmonary hypertension, according to the present invention, a treatment by inhalation may also be chosen; in this case, the inhaled doses are smaller.

Although these doses are examples of average situations, there may be particular cases in which higher or lower doses are appropriate, and such doses also form part of the invention. According to the usual practice, the dosage that is appropriate for each patient is determined by the doctor according to the mode of administration, the age, the weight and the response of said patient.

When a solid composition in the form of tablets or gel capsules is prepared, a mixture of pharmaceutical excipients is added to the active principles, which may or may not be micronized, this mixture possibly being composed of diluents, for instance lactose, mannitol, microcrystalline cellulose, starch or dicalcium phosphate, binders, for instance polyvinylpyrrolidone or hydroxypropylmethylcellulose, disintegrating agents such as crosslinked polyvinylpyrrolidone, crosslinked carboxymethylcellulose or sodium croscarmellose, glidants, for instance silica or talc, and lubricants, for instance magnesium stearate, stearic acid, glyceryl tribehenate or sodium stearylfumarate.

Wetting agents or surfactants such as sodium lauryl sulfate, polysorbate 80 or poloxamer 188 may be added to the formulation.

The tablets may be made via various techniques: direct compression, dry granulation, wet granulation or hot-melting.

The tablets may be plain or sugar-coated (for example with sucrose) or coated with various polymers or other suitable materials.

The tablets may have a flash, delayed or sustained release by making polymer matrices or by using specific polymers in the film coating.

The gel capsules may be soft or hard, and uncoated or film-coated so as to have flash, sustained or delayed activity (for example via a gastroresistant form). They may contain not only a solid formulation formulated as above for the tablets, but also liquids or semisolids.

A preparation in syrup or elixir form may contain the active principle(s) together with a sweetener, preferably a calorie-free sweetener, methylparaben and propylparaben as antiseptics, and also a flavor enhancer and a suitable dye.

The water-dispersible powders or granules may contain the active principle(s) as a mixture with dispersants or wetting agents, or suspension agents, for instance polyvinylpyrrolidone or polyvidone, and also with sweeteners or flavor enhancers.

For rectal administration, use is made of suppositories, which are prepared with binders that melt at the rectal temperature, for example cocoa butter or polyethylene glycols.

For parenteral, intranasal or intraocular administration, aqueous suspensions, isotonic saline solutions or sterile injectable solutions containing pharmacologically compatible dispersants and/or solubilizing agents, for example propylene glycol or butylene glycol, are used.

Thus, to prepare an aqueous solution for intravenous injection, it is possible to use a cosolvent, for example an alcohol such as ethanol or a glycol such as polyethylene glycol or propylene glycol, and a hydrophilic surfactant such as polysorbate 80 or poloxamer 188. To prepare an oily solution for intramuscular injection, the active principle may be dissolved with a triglyceride or a glycerol ester.

Creams, ointments, gels, eye drops or sprays may be used for local administration.

Patches in multilaminar or reservoir form in which the active principle is in alcoholic solution may be used for transdermal administration.

An aerosol containing, for example, sorbitan trioleate or oleic acid and also trichlorofluoromethane, dichlorofluoromethane, dichlorotetrafluoroethane, freon substitutes or any other biologically compatible propellent gas is used for administration by inhalation; a system containing the active principle alone or combined with an excipient, in powder form, may also be used.

The active principles may also be in the form of a complex with a cyclodextrin, for example α-, β- or γ-cyclodextrin, 2-hydroxypropyl-β-cyclodextrin or methyl-β-cyclodextrin.

The active principle(s) may also be formulated in the form of microcapsules or microspheres, optionally with one or more supports or additives.

Among the sustained-release forms that are useful in the case of chronic treatments, use may be made of implants. These may be prepared in the form of an oily suspension or in the form of a suspension of microspheres in an isotonic medium.

Preferably, the irbesartan is administered orally, as a single dosage intake per day or by inhalation using an aerosol, one or more times a day.

According to another of its aspects, the invention also relates to a method that consists in administering a therapeutically effective amount of irbesartan, a pharmaceutically acceptable salt thereof or a solvate thereof.

EXPERIMENTAL PROTOCOL

Male Sprague-Dawley rats weighing about 300 g received a subcutaneous injection of monocrotaline (MCT) at a dose of 80 mg/kg.

The treatment with irbesartan was started either 21 days or 14 days after injection of monocrotaline. Irbesartan was incorporated into the food in powder form. The control animals received food alone.

Throughout the study, the animals were examined daily.

In a first study, irbesartan was administered alone at a dose of 50 mg/kg. In a second study, irbesartan was administered alone at a dose of 30 mg/kg and in combination with hydrochlorothiazide (HCTZ): irbesartan: 30 mg/kg and HCTZ: 10 mg/kg.

Study 1:

Results

Treatment started on the 21st day:

| Groups | Survival to the 25th day | Survival to the 50th day | Survival to the end of the study (57th day) |
|---|---|---|---|
| Controls | 100% (18/18) | 33% (6/18) | 17% (3/18) |
| Irbesartan 50 mg/kg | 100% (18/18) | 72% (13/18) | 61% (11/18) |
|  | — | p = 0.043 | p = 0.015 |

Treatment started on the 14th day:

| Groups | Survival to the 25th day | Survival to the 50th day | Survival to the end of the study (100th day) |
|---|---|---|---|
| Controls | 100% (12/12) | 33% (4/12) | 0% (0/12) |
| Irbesartan 50 mg/kg | 100% (12/12) | 83% (10/12) | 50% (6/12) |
|  | — | p = 0.036 | p = 0.014 |

Irbesartan, administered at a dose of 50 mg/kg/day, either from the 21st day or from the 14th day post-MCT, significantly increased the survival time of the MCT-treated rats.

When the treatment was started on the 21st day, it was observed at the end of the study that 17% of the control animals were still alive, versus 61% of the irbesartan-treated animals (p=0.0153, Fisher test). Furthermore, in the treated group, a significant increase is seen in the survival time from the 35th day relative to the control group (p=0.0160, log-rank test).

When the treatment was started on the 14th day, at the end of the study, whereas all the control animals were dead, 50% of the irbesartan-treated animals were still alive (p=0.014, Fisher test). Furthermore, a significant increase is seen in the overall survival time estimated in the treated group (>93 days) compared with the control group (46 days) (p=0.0001, log-rank test).

Study 2:

Results

Treatment started on the 14th day:

| Groups | Survival to the 50th day | Survival to the end of the study (85th day) |
|---|---|---|
| Controls | 16.7% (4/24) | 4.2% (1/24) |
| Irbesartan 30 mg/kg | 47.8% (11/23) | 0% (0/23) |
| HCTZ 10 mg/kg | 25% (6/24) | 4.2% (1/24) |
| Irbesartan 30 mg/kg HCTZ 10 mg/kg | 60.9% (14/23) | 39.1% (9/23) |

This study, performed at a lower dose of irbesartan than the first study, demonstrates an increase in the survival time at the end of the study for the animals treated with the irbesartan+HCTZ combination, compared with irbesartan alone (p=0.0015, Fisher test). The median estimated survival time is 70 days for the animals treated with the combination, versus 46 days for the animals treated with irbesartan alone (p=0.0033, log-rank test).

This set of results demonstrates a beneficial effect of irbesartan on mortality consecutive to pulmonary hypertension induced by injection of monocrotaline in rats. This beneficial effect is potentiated when the irbesartan is coadministered with a diuretic agent such as hydrochlorothiazide.

EXAMPLES OF TABLETS

|  | EXAMPLE 1 | EXAMPLE 2 | EXAMPLE 3 |
|---|---|---|---|
| Irbesartan | 75.00 mg | 150.00 mg | 300.00 mg |
| Lactose monohydrate | 15.38 mg | 30.75 mg | 61.50 mg |
| Microcrystalline cellulose | 19.50 mg | 39.00 mg | 78.00 mg |
| Pregelatinized corn starch | 22.50 mg | 45.00 mg | 90.00 mg |
| Sodium croscarmellose | 7.50 mg | 15.00 mg | 30.00 mg |
| Poloxamer 188 | 4.50 mg | 9.00 mg | 18.00 mg |
| Hydrated colloidal silica | 4.12 mg | 8.25 mg | 16.50 mg |
| Magnesium stearate | 1.50 mg | 3.00 mg | 6.00 mg |
| Purified water | qs | qs | qs |
|  | 150.00 mg | 300.00 mg | 600.00 mg |

-continued

|  | EXAMPLE 4 | EXAMPLE 5 |
|---|---|---|
| Irbesartan | 150.00 mg | 300.00 mg |
| Hydrochlorothiazide | 12.50 mg | 12.50 mg |
| Lactose monohydrate | 26.65 mg | 65.80 mg |
| Microcrystalline cellulose | 45.00 mg | 90.00 mg |
| Pregelatinized corn starch | 45.00 mg | 90.00 mg |
| Sodium croscarmellose | 15.00 mg | 30.00 mg |
| Red iron oxide | 0.30 mg | 0.60 mg |
| Yellow iron oxide | 0.30 mg | 0.60 mg |
| Hydrated colloidal silica | 2.25 mg | 4.50 mg |
| Magnesium stearate | 3.00 mg | 6.00 mg |
| Purified water | qs | qs |
|  | 300.00 mg | 600.00 mg |

Example 6

| Micronized irbesartan | 4 mg |
|---|---|
| Lactose | qs 20 mg |

For a powder inhalation device, composed of 7 disks of 8 doses, each weighing 20 mg.

Example 7

| Micronized irbesartan | 1 mg |
|---|---|
| Lactose | qs 6 mg |

For a powder inhalation device, containing a cartridge of 12 alveolae, each containing 4 mg of formulation.

Example 8

| Micronized irbesartan | 4 mg |
|---|---|
| Lactose 50 microns | qs 20 mg |

For a finished size 3 gel capsule weighing 20 mg. Box of 30 gel capsules. Powder inhalation device.

Example 9

| Micronized irbesartan | 600 mg |
|---|---|
| Freon 12 | 14 g |

For a pressurized flask with a metering valve, containing 150 doses.

Example 10

| Micronized irbesartan | 600 mg |
|---|---|
| Freon 11 | 4.7 g |
| Freon 12 | 9.8 g |

For a pressurized flask with a metering valve, containing 150 doses.

Example 11

| Micronized irbesartan | 300 mg |
|---|---|
| HFA (hydrofluoroalkane) 134a | 13 g |
| Sorbitan trioleate | 30 mg |

For a pressurized flask with a metering valve, containing 150 doses.

Example 12

| Micronized irbesartan | 300 mg |
|---|---|
| Freon 11 | 4.7 g |
| Freon 12 | 9.8 g |
| Oleic acid | 40 mg |

For a pressurized flask with a metering valve, containing 150 doses.

Example 13

| Micronized irbesartan | 600 mg |
|---|---|
| HCTZ | 25 mg |
| Freon 12 | 14 g |

For a pressurized flask with a metering valve, containing 150 doses.

Example 14

| Micronized irbesartan | 300 mg |
|---|---|
| HCTZ | 25 mg |
| HFA (hydrofluoroalkane) | 13 g |
| Sorbitan trioleate | 30 mg |

For a pressurized flask with a metering valve, containing 150 doses.

The invention claimed is:
1. A method for treating pulmonary arterial hypertension or pulmonary hypertension, the method comprising administering to a patient in need of such treatment an effective amount of irbesartan.
2. The method according to claim 1, wherein said irbesartan is combined with hydrochlorothiazide.

* * * * *